US00PP24679P2

(12) United States Plant Patent
Isobe

(10) Patent No.: US PP24,679 P2
(45) Date of Patent: Jul. 22, 2014

(54) ***PETUNIA* PLANT NAMED 'SUNSURF PIUSA'**

(50) Latin Name: *Petunia×hybrida*
Varietal Denomination: Sunsurf Piusa

(71) Applicant: Yasuko Isobe, Shiga (JP)

(72) Inventor: Yasuko Isobe, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 42 days.

(21) Appl. No.: 13/694,018

(22) Filed: Oct. 20, 2012

(51) Int. Cl.
*A01H 5/00* (2006.01)

(52) U.S. Cl.
USPC ..... Plt./356.22

(58) Field of Classification Search
CPC ..... A01H 5/02
USPC ..... Plt./356.22, 356.13
See application file for complete search history.

*Primary Examiner* — Kent L Bell
(74) *Attorney, Agent, or Firm* — C. A. Whealy

(57) ABSTRACT

A new and distinct cultivar of *Petunia* plant named 'Sunsurf Piusa', characterized by its compact and mounding plant habit; vigorous growth habit; freely branching habit; early and freely flowering habit; long flowering period; small bright red purple-colored flowers; and good garden performance.

1 Drawing Sheet

Botanical designation: *Petunia×hybrida*.
Cultivar denomination: 'SUNSURF PIUSA'.

BACKGROUND OF THE INVENTION

The present invention relates to a new and distinct cultivar of *Petunia* plant, botanically known as *Petunia×hybrida* and hereinafter referred to by the name 'Sunsurf Piusa'.

The new *Petunia* plant is a product of a planned breeding program conducted by the Inventor in Higashiomi, Shiga, Japan. The objective of the breeding program is to create new compact, freely branching and freely flowering *Petunia* plants with mounding habit and attractive flower coloration.

The new *Petunia* plant originated from a cross-pollination made by the Inventor in January, 2005 in Higashiomi, Shiga, Japan of a proprietary selection of *Petunia×hybrida* identified as code name Px139-02, not patented, as the female, or seed, parent with a proprietary selection of *Petunia×hybrida* identified as code name BR-01, not patented, as the male, or pollen, parent. The new *Petunia* plant was discovered and selected by the Inventor as a single flowering plant within the progeny of the stated cross-pollination in a controlled greenhouse environment in Higashiomi, Shiga, Japan in November, 2007.

Asexual reproduction of the new *Petunia* plant by terminal cuttings in a controlled greenhouse environment in Higashiomi, Shiga, Japan since November, 2007 has shown that the unique features of this new *Petunia* plant are stable and reproduced true to type in successive generations.

SUMMARY OF THE INVENTION

Plants of the new *Petunia* have not been observed under all possible environmental conditions and cultural conditions. The phenotype may vary somewhat with variations in environmental conditions such as temperature and light intensity without, however, any variance in genotype.

The following traits have been repeatedly observed and are determined to be the unique characteristics of 'Sunsurf Piusa'. These characteristics in combination distinguish 'Sunsurf Piusa' as a new and distinct *Petunia* plant:

1. Compact and mounding plant habit.
2. Vigorous growth habit.
3. Freely branching habit.
4. Early and freely flowering habit.
5. Long flowering period.
6. Small bright red purple-colored flowers.
7. Good garden performance.

Plants of the new *Petunia* can be compared to plants of the female parent selection. Plants of the new *Petunia* differ primarily from plants of the female parent selection in flower color as plants of the female parent selection have dark red purple-colored flowers.

Plants of the new *Petunia* can be compared to plants of the male parent selection. Plants of the new *Petunia* differ primarily from plants of the male parent selection in the following characteristics:

1. Plants of the new *Petunia* are more compact than plants of the male parent selection.
2. Plants of the new *Petunia* have larger flowers than plants of the male parent selection.

Plants of the new *Petunia* can also be compared to plants of the *Petunia* 'Sunsurfcoparu', disclosed in U.S. Plant Pat. No. 18,141. In side-by-side comparisons conducted in Higashiomi, Shiga, Japan, plants of the new *Petunia* and 'Sunsurfcoparu' differed primarily in the following characteristics:

1. Plants of the new *Petunia* were taller than plants of 'Sunsurfcoparu'.
2. Plants of the new *Petunia* had shorter internodes than plants of 'Sunsurfcoparu'.
3. Plants of the new *Petunia* had slightly larger leaves with longer petioles than plants of 'Sunsurfcoparu'.
4. Plants of the new *Petunia* had larger flowers than plants of 'Sunsurfcoparu'.
5. Flowers of plants of the new *Petunia* were longer lasting than flowers of plants of 'Sunsurfcoparu'.

6. Petal apices of plants of the new *Petunia* were mucronate in shape whereas petal apices of plants of 'Sunsurfcoparu' were truncate in shape.
7. Plants of the new *Petunia* and 'Sunsurfcoparu' differed in flower color as plants of 'Sunsurfcoparu' had pink-colored flowers.
8. Plants of the new *Petunia* had shorter peduncles than plants of 'Sunsurfcoparu'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet comprises a side perspective view of a typical flowering plant of 'Sunsurf Piusa' grown in a container.

The photograph at the bottom of the sheet is a close-up view of a typical flowering plant of 'Sunsurf Piusa'.

DETAILED BOTANICAL DESCRIPTION

The aforementioned photographs and following observations, measurements and values describe plants grown during the late summer in 15-cm containers in an outdoor nursery in Higashiomi, Shiga, Japan and under cultural practices typical of commercial *Petunia* production. During the production of the plants, day temperatures averaged 23° C. and night temperatures averaged 13° C. Plants were two months old when the photographs were taken, and plants were five months old when the description was taken. In the following description, color references are made to The Royal Horticultural Society Colour Chart, 2007 Edition, except where general terms of ordinary dictionary significance are used.

Botanical classification: *Petunia×hybrida* 'Sunsurf Piusa'.

Parentage:

*Female, or seed, parent*.—Proprietary selection of *Petunia×hybrida* identified as code name Px139-02, not patented.

*Male, or pollen, parent*.—Proprietary selection of *Petunia×hybrida* identified as code name BR-01, not patented.

Propagation:

*Type*.—By terminal cuttings.

*Time to initiate roots, summer and winter*.—About one week at temperatures of about 15° C. to 20° C.

*Time to produce a rooted young plant, summer and winter*.—About three weeks at temperatures of about 15° C. to 20° C.

*Root description*.—Fibrous; white in color.

*Rooting habit*.—Freely branching; dense.

Plant description:

*Plant and growth habit*.—Compact and mounding plant habit; freely branching habit with numerous lateral branches developing per plant; pinching enhances lateral branch development; vigorous growth habit.

*Plant height*.—About 20.5 cm.

*Plant diameter*.—About 33 cm.

Lateral branch description:

*Length*.—About 18 cm.

*Diameter*.—About 1.5 mm.

*Internode length*.—About 1.4 cm.

*Strength*.—Strong, flexible.

*Aspect*.—Upright to somewhat outwardly.

*Texture*.—Densely pubescent.

*Color*.—Close to 143A.

Foliage description:

*Arrangement*.—Alternate, simple.

*Length*.—About 4.7 cm.

*Width*.—About 2.8 cm.

*Shape*.—Ovate.

*Apex*.—Broadly acute.

*Base*.—Attenuate.

*Margin*.—Entire.

*Texture, upper and lower surfaces*.—Densely pubescent.

*Venation pattern*.—Pinnate; reticulate.

*Color*.—Developing and fully expanded leaves, upper surface: Close to 137B; venation, close to 143C. Developing and fully expanded leaves, lower surface: Close to 137D; venation, close to 143C.

*Petioles*.—Length: About 1.4 mm. Diameter: About 1.1 mm. Texture, upper and lower surfaces: Densely pubescent. Color, upper and lower surfaces: Close to 143C.

Flower description:

*Flower arrangement and habit*.—Single salverform flowers arising from upper leaf axils; freely flowering habit with usually about 28 flowers developing per plant; flowers face upright to somewhat outwardly.

*Fragrance*.—None detected.

*Natural flowering season*.—Early flowering habit, plants of the new *Petunia* initiate and develop flowers about two weeks after planting; long flowering period; flowering commences naturally during the spring and plants flower continuously throughout the summer until late autumn in Japan.

*Flower longevity*.—Individual flowers last about seven to ten days on the plant; flowers not persistent.

*Flower diameter*.—About 4.9 cm.

*Flower length (depth)*.—About 3.7 cm.

*Throat diameter*.—About 1.1 cm.

*Tube diameter, base*.—About 2.2 mm.

*Tube length*.—About 3 cm.

*Flower buds*.—Length: About 3.7 cm. Diameter: About 6.1 mm. Shape: Cylindrical. Color: Close to 149D; towards the apex, close to N78B.

*Corolla*.—Arrangement: Five petals fused at the base and opening into a flared trumpet. Petal length from throat: About 2.3 cm. Petal width: About 2.3 cm. Petal shape: Spatulate. Petal apex: Mucronate. Petal margin: Entire, undulate. Petal texture, upper and lower surfaces: Smooth; glabrous. Throat texture: Smooth, glabrous. Tube texture: Smooth, glabrous. Color: Petal, when opening, upper surface: Close to 72A; venation, close to 72A. Petal, when opening, lower surface: Close to 72B; venation, close to 72B. Petal, fully opened, upper surface: Close to N74A; venation, close to N74A. Petal, fully opened, lower surface: Close to 72C; venation, close to 72C. Throat: Close to 2D; proximally, close to. 2C; venation, close to 2D and 2C. Tube: Close to 145D; venation, close to 145D.

*Calyx*.—Arrangement: One star-shaped calyx tube with five sepals in a single whorl and fused at the base. Sepal length: About 1.2 cm. Sepal width: About 1.8 mm. Sepal shape: Narrowly elliptic. Sepal apex:

Obtuse. Sepal margin: Entire. Sepal texture, upper and lower surfaces: Pubescent. Color: Developing and fully opened sepals, upper surface: Close to 143B. Developing and fully opened sepals, lower surface: Close to 143B.

*Peduncles*.—Length: About 1.7 cm. Diameter: About 1.1 mm. Strength: Strong. Texture: Pubescent. Color: Close to 143B.

*Reproductive organs*.—Stamens: Quantity per flower: Five. Stamen length: About 1.4 cm to 2 cm. Anther shape: Ellipsoidal. Anther size: About 1.3 mm by 1.6 mm. Anther color: Close to 155C. Pollen amount: Abundant. Pollen color: Close to 155D. Pistils: Quantity per flower: One Pistil length: About 1.8 cm. Style color: Close to 145B. Stigma shape: Transversely ellipsoidal. Stigma color: Close to 145A. Ovary color: Close to N144C. Seeds and fruits: Seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen & pest resistance: Plants of the new *Petunia* have not been observed to be resistant to pathogens and pests common to *Petunia* plants.

It is claimed:

1. A new and distinct *Petunia* plant named 'Sunsurf Piusa' as illustrated and described.

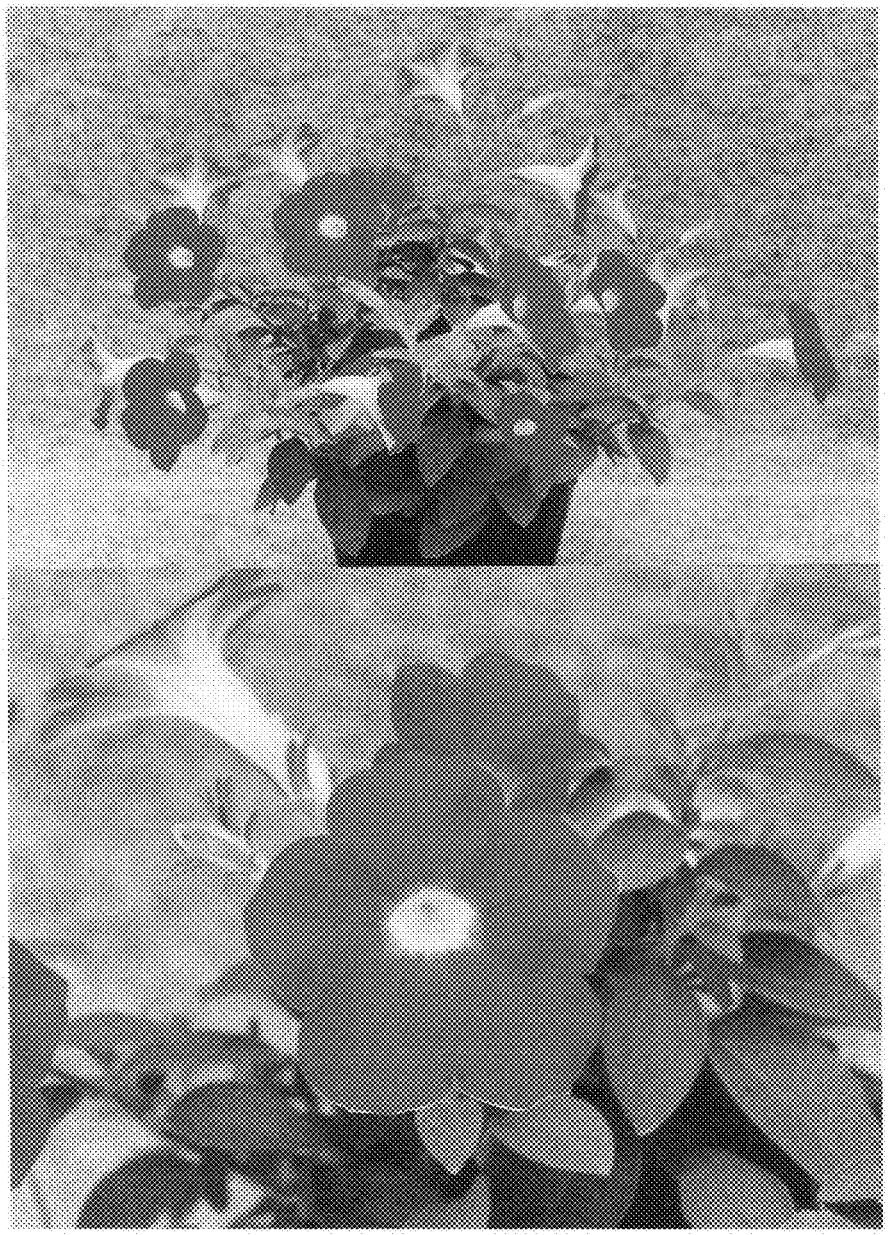

* * * * *